(12) United States Patent
Shimizu

(10) Patent No.: US 10,569,048 B2
(45) Date of Patent: Feb. 25, 2020

(54) JUNCTION STRUCTURE AND CATHETER HAVING THE JUNCTION STRUCTURE

(71) Applicant: ASAHI INTECC CO., LTD., Seto-shi, Aichi (JP)

(72) Inventor: Yusuke Shimizu, Owariasahi (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 0 days.

(21) Appl. No.: 15/640,803

(22) Filed: Jul. 3, 2017

(65) Prior Publication Data

US 2018/0056032 A1 Mar. 1, 2018

Related U.S. Application Data

(63) Continuation of application No. PCT/JP2016/074490, filed on Aug. 23, 2016.

(51) Int. Cl.
 *A61M 25/00* (2006.01)
 *A61M 39/10* (2006.01)

(52) U.S. Cl.
 CPC ...... *A61M 25/005* (2013.01); *A61M 25/0054* (2013.01); *A61M 39/10* (2013.01); *A61M 25/0009* (2013.01); *A61M 2039/1027* (2013.01)

(58) Field of Classification Search
 CPC ............ A61M 25/001; A61M 25/0012; A61M 25/005; A61M 25/0041; A61M 25/0043; A61M 25/002; A61M 25/0054; A61M 39/10; A61M 2039/1027; A61M 25/0009
 See application file for complete search history.

(56) References Cited

U.S. PATENT DOCUMENTS

| 5,160,559 A | 11/1992 | Scovil et al. |
| 5,403,292 A * | 4/1995 | Ju .......................... A61L 29/049 600/435 |
| 5,584,821 A | 12/1996 | Hobbs et al. |

(Continued)

FOREIGN PATENT DOCUMENTS

| JP | H9-512445 A | 12/1997 |
| JP | H11-239617 A | 9/1999 |

(Continued)

OTHER PUBLICATIONS

Oct. 4, 2017 Office Action issued in Japanese Patent Application No. 2017-510595.

(Continued)

*Primary Examiner* — Brandy S Lee
(74) *Attorney, Agent, or Firm* — Oliff PLC

(57) ABSTRACT

Provided is a junction structure between a first tubular member and a second tubular member, and a catheter including the junction structure. An interface between the first tubular member and the second tubular member has an uneven shape in the longitudinal direction of the junction structure along a circumferential direction of the first tubular member and the second tubular member. At least one of the first tubular member and the second tubular member includes a protruding portion that protrudes into the other tubular member only between an inner periphery of the other tubular member and an outer periphery of the other tubular member. The joining strength of the junction structure is improved against a pressure in the radial direction.

10 Claims, 12 Drawing Sheets

(56) References Cited

U.S. PATENT DOCUMENTS

| | | | |
|---|---|---|---|
| 5,662,622 A * | 9/1997 | Gore | A61M 25/0012 |
| | | | 138/123 |
| 5,792,124 A * | 8/1998 | Horrigan | A61M 25/001 |
| | | | 604/265 |
| 6,007,478 A | 12/1999 | Siess et al. | |
| 6,027,528 A * | 2/2000 | Tomonto | A61L 27/04 |
| | | | 623/1.49 |
| 6,103,037 A | 8/2000 | Wilson | |
| 2014/0114288 A1* | 4/2014 | Beasley | A61M 25/0054 |
| | | | 604/525 |

FOREIGN PATENT DOCUMENTS

| | | |
|---|---|---|
| JP | 2004-301197 A | 10/2004 |
| JP | 2005-334542 A | 12/2005 |
| JP | 2013-533767 A | 8/2013 |
| WO | 95/028982 A1 | 11/1995 |
| WO | 97/14466 A1 | 4/1997 |
| WO | 2011/159955 A1 | 12/2011 |

OTHER PUBLICATIONS

Nov. 20, 2017 Office Action issued in Japanese Patent Application No. 2017-510595.

Nov. 22, 2016 International Search Report issued in International Patent Application No. PCT/JP2016/074490.

Nov. 22, 2016 Written Opinion of the International Searching Authority issued in International Patent Application No. PCT/JP2016/074490.

* cited by examiner

JUNCTION STRUCTURE AND CATHETER HAVING THE JUNCTION STRUCTURE

CROSS REFERENCE TO RELATED APPLICATION

This application is a continuation of PCT/JP2016/074490 filed on Aug. 23, 2016, the contents of which are incorporated by reference herein in their entirety.

BACKGROUND

The disclosed embodiments relate to a medical device. Specifically, the disclosed embodiments relate to a junction structure for joining corresponding end portions of two tubular members, and a catheter having the junction structure.

A catheter to be inserted into a lumen in the body such as blood vessel, ureter, and the like of a patient at the time of procedure generally includes a tube member, a distal end tip joined to a distal end of the tube member, and a connector joined to a proximal end of the tube member.

Further, in such a catheter, the tube member is formed from multiple tubular members each having a different hardness. The tubular members are provided in series in order of decreasing hardness toward a distal end of the catheter in order to gradually increase the flexibility of the catheter toward its distal end.

For a tube member of a catheter manufactured by sequentially joining multiple tubular members as described above, the joined tubular members need to have sufficient joining strength to prevent the joined tubular members from detaching from each other even when the catheter is inserted into a body lumen of a patient and is bent along the curvature of the body lumen.

For example, Japanese Patent Application Laid-Open No. 2005-334542 describes medical tubes used for medical devices such as catheters, in which a joining area between the medical tubes is increased at each end of the medical tubes to enhance their joining strength when corresponding ends of the medical tubes are joined (see FIG. 1 and others).

However, in the medical tubes described in Japanese Patent Application Laid-Open No. 2005-334542, the joining strength is weak against a pressure in the radial direction. This may result in the following disadvantages: for example, when the medical tubes are joined via tapered portions formed at each end portion of the medical tubes (see FIG. 3(b)), the joined tapered portions are susceptible to forming cracks when the medical tubes are bent; and when the medical tubes are joined via stepped portions formed at each of the end portions (see FIG. 5), the joined stepped portions are also susceptible to forming cracks when the medical tubes are bent.

SUMMARY

The disclosed embodiments have been devised to address the above problems. An object of the disclosed embodiments is to provide a junction structure in which the joining strength thereof is further improved against a pressure in the radial direction. Another object of the disclosed embodiments is to provide a catheter having the above junction structure.

In order to achieve the above object, the disclosed embodiments include a junction structure formed between a first tubular member made of resin and a second tubular member made of resin, in which an interface between the first tubular member and the second tubular member has an uneven shape in the long axis direction along the circumferential direction, and any one of the first tubular member and the second tubular member may include a protruding portion that protrudes into the other tubular member only between an inner periphery and an outer periphery of the other tubular member in a cross sectional view. This configuration enhances the joining strength between the first tubular member and the second tubular member against a pressure in the radial direction. It also increases the joining area, which further enhances the joining strength between the first tubular member and the second tubular member.

The protruding portion may have a convex shape. In this configuration, the protruding portion is prevented from projecting out of the other tubular member.

The disclosed embodiments include a catheter having the junction structure. The catheter may include an inner layer, a reinforcing layer (a braid or a coil body) disposed around an outer periphery of the inner layer, and outer layers covering outer peripheries of the inner layer and the reinforcing layer. The outer layers are joined by the junction structure described above, and an inner periphery of the other tubular member (into which the protruding portion protrudes) penetrates into the reinforcing layer. This configuration further enhances the joining strength between the first tubular member and the second tubular member.

DETAILED DESCRIPTION OF EMBODIMENTS

Below, embodiments of the present invention will be described with reference to the drawings.

Figure 1:
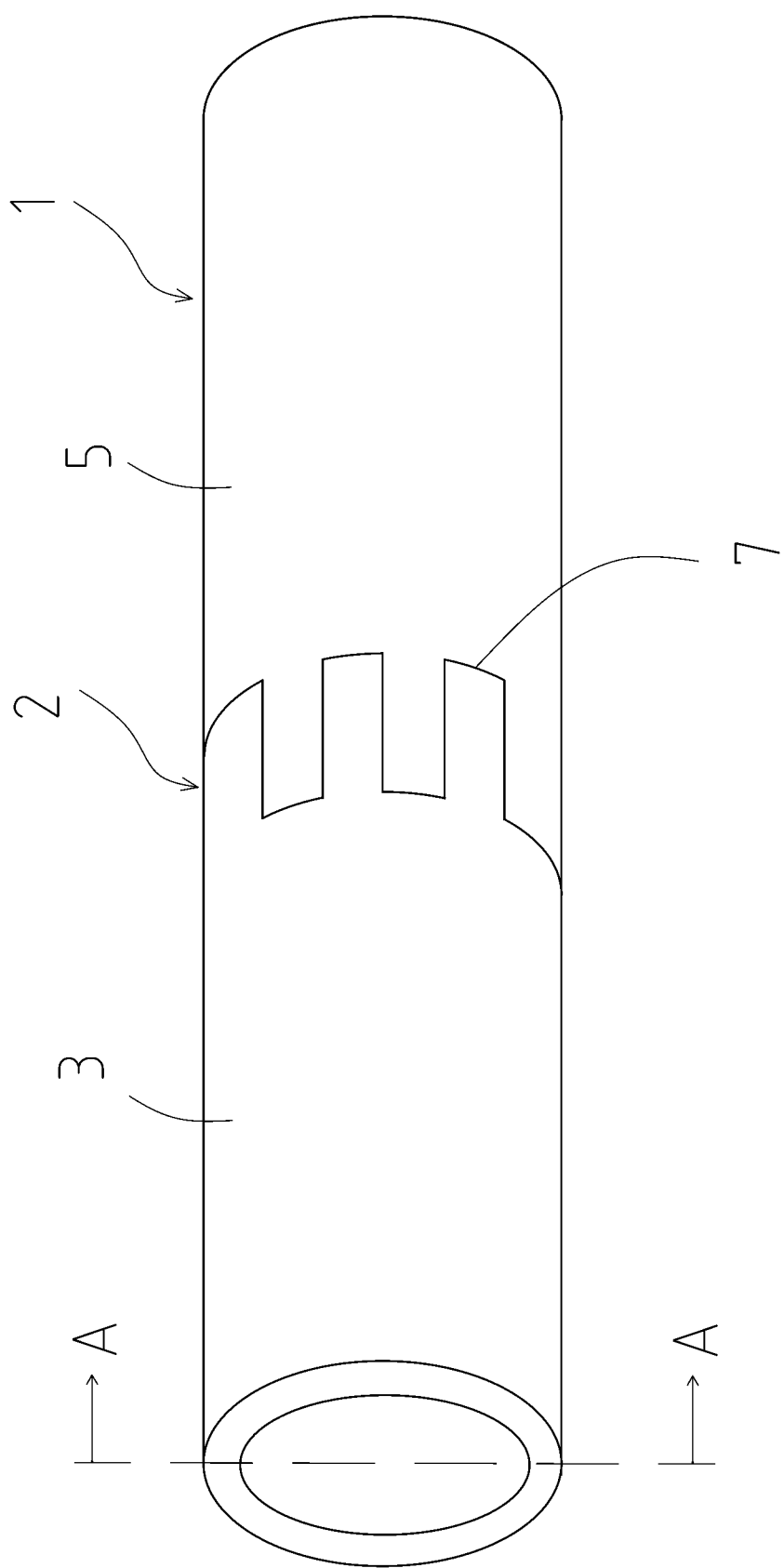
FIG. 1 shows a perspective view of a junction structure according to the disclosed embodiments.
Figure 2:
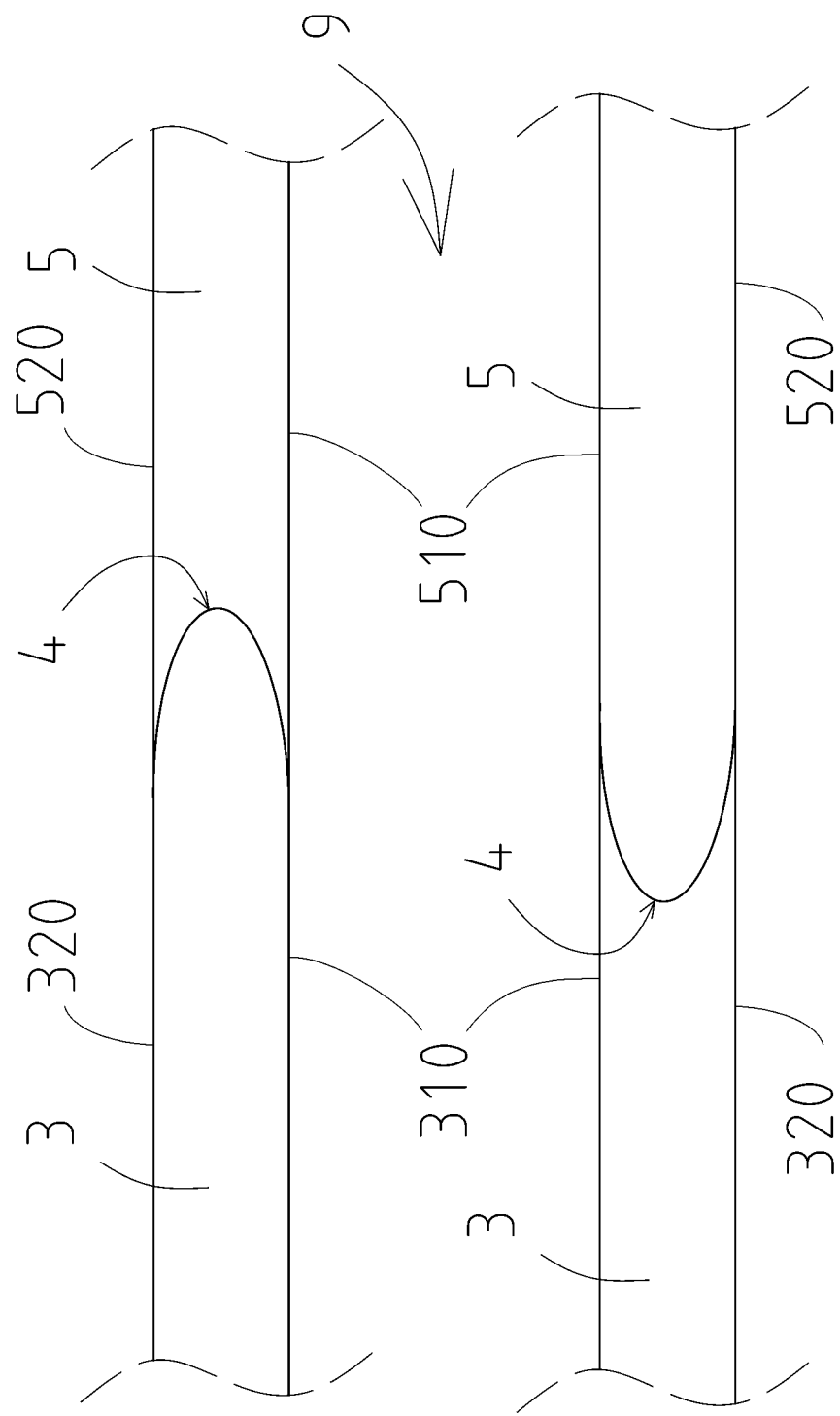
FIG. 2 shows a cross sectional view near a joining region when the junction structure of FIG. 1 is cut in the direction of line A-A shown in FIG. 1.
Figure 3:
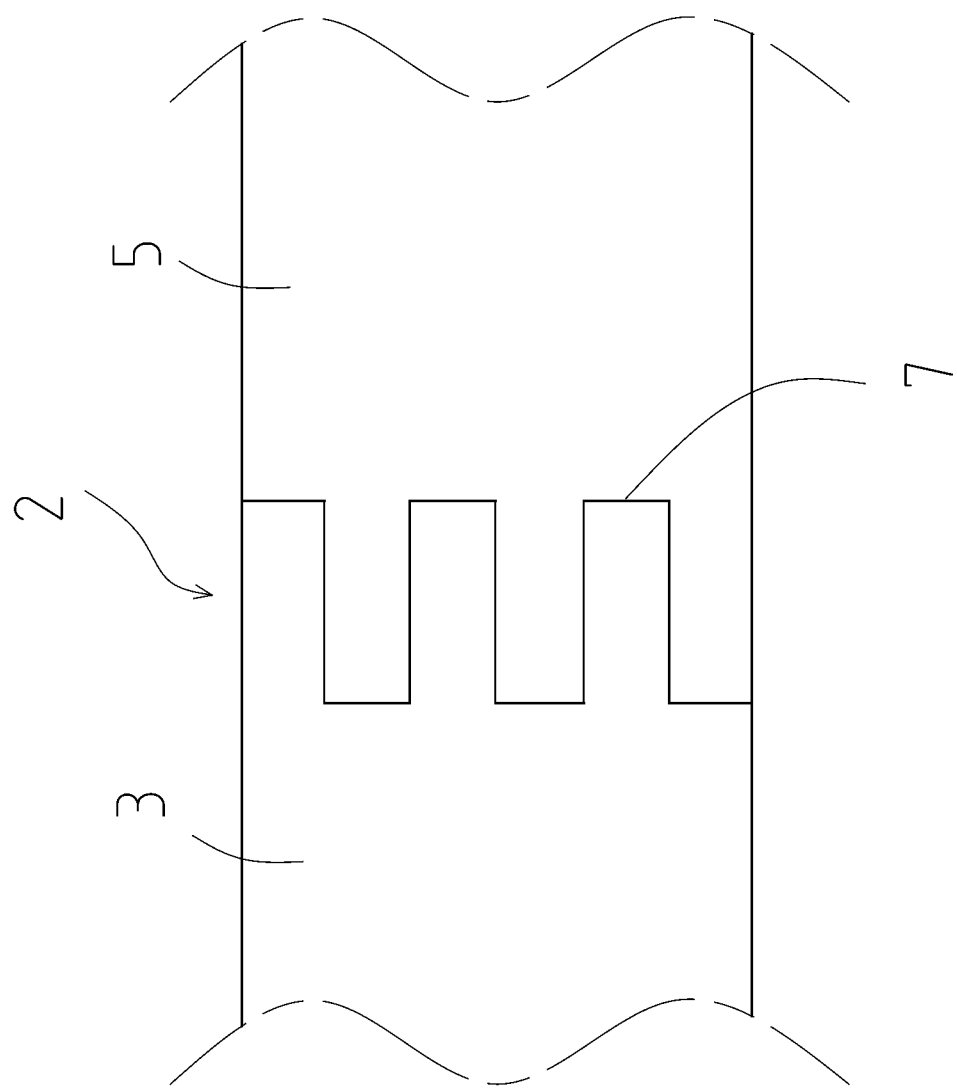
FIG. 3 shows a side view near the joining region of the junction structure shown in FIG. 1.
Figure 4:
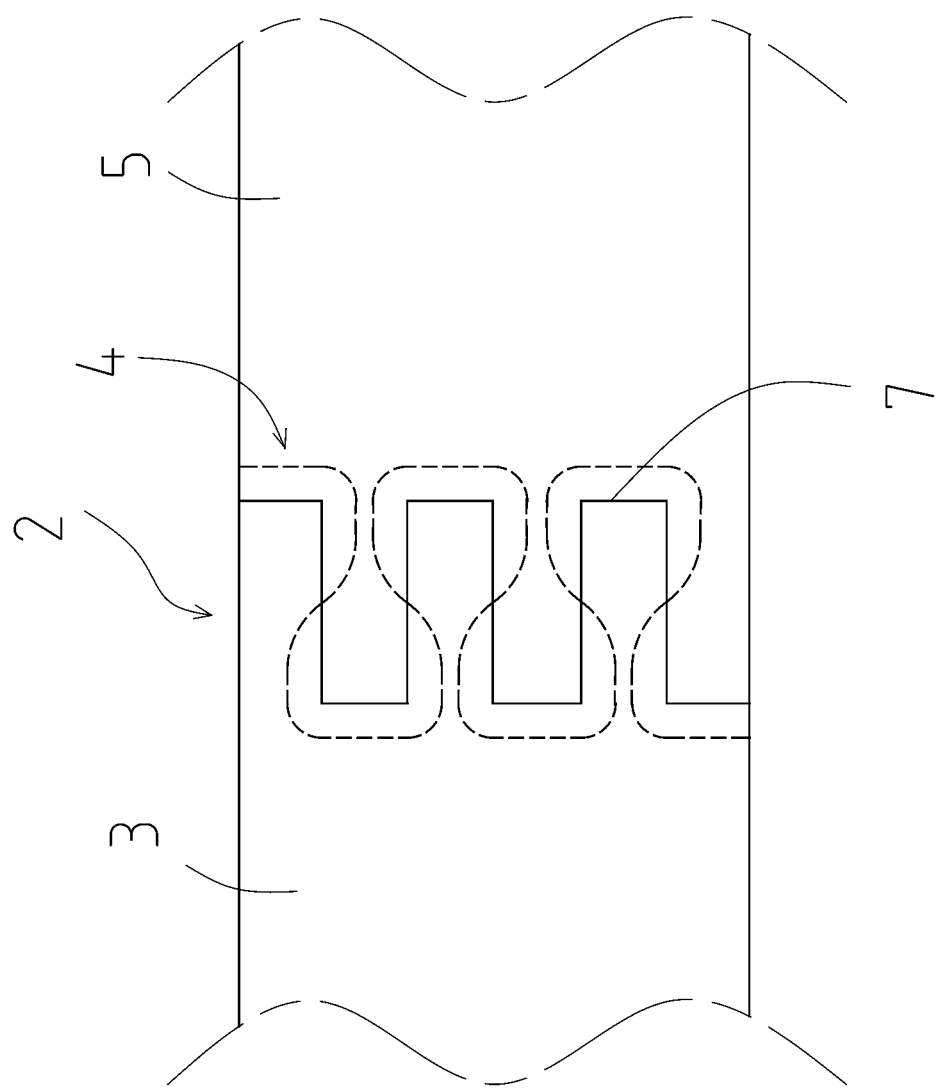
FIG. 4 shows the side view of FIG. 3 with an inner protruding portion shown in dotted lines.

FIG. 1 shows a perspective view of a junction structure according to the disclosed embodiments, and FIG. 2 shows a cross sectional view near a joining region when the junction structure of FIG. 1 is cut in the direction of line A-A. FIG. 3 shows a side view near the joining region of the junction structure shown in FIGS. 1 and 2, and FIG. 4 shows the side view of FIG. 3 with an inner protruding portion shown in dotted lines.

With reference to FIG. 1, a tubular member 3 and a tubular member 5 are joined at a junction structure 1. The tubular member 3 and the tubular member 5 may each be made of resin. An interface 7 between the tubular member 3 and the tubular member 5 at a joining region 2 has an uneven shape in the long axis (longitudinal) direction along the circumferential direction of the tubular members. That is, a distance from the interface 7 to a plane normal to the tubular members 3, 5 varies along the circumference of each of the tubular member 3 and the tubular member 5.

In FIG. 1, the uneven shape includes approximately rectangular protrusions along the circumferential direction of the tubular members 3, 5.

Here, the interface 7 between the tubular member 3 and the tubular member 5 is configured to have an uneven shape in the long axis direction along the circumferential direction of the tubular members 3, 5 in order to increase a joining area between the tubular member 3 and the tubular member 5 as much as possible. This improves the joining strength between the tubular member 3 and the tubular member 5.

FIG. 2 shows a cross sectional view near the joining region 2 when the junction structure 1 shown in FIG. 1 is cut in the direction of line A-A. With reference to FIG. 2, the tubular member 3 and the tubular member 5 each have an inner cavity 9, the inner cavities 9 communicating with each other. At the interface 7 between the tubular member 3 and the tubular member 5, the tubular member 3 includes a protruding portion 4 that protrudes into the tubular member 5 only between an inner circumferential surface 510 (an inner periphery) and an outer circumferential surface 520 (an outer periphery) of the tubular member 5 (i.e., in a region other than the inner and outer edges of the tubular member 5) in the upper portion of the figure, and the tubular member 5 includes a protruding portion 4 that protrudes into the tubular member 3 only between an inner circumferential surface 310 (an inner periphery) and an outer circumferential surface 320 (an outer periphery) of the tubular member 3 in the lower portion of the figure.

In FIG. 2, the protruding portion 4 of each of the tubular member 3 and the tubular member 5 has a convex shape.

Here, at least one of the tubular member 3 and the tubular member 5 includes the protruding portion 4 that protrudes into the other tubular member (only between an inner periphery and an outer periphery of the other tubular member) in order to improve the joining strength between the tubular member 3 and the tubular member 5 when a force is applied to the interface 7 between the tubular member 3 and the tubular member 5 in the radial direction (the outward or inward direction from a longitudinal axis of the tubular member, i.e., the vertical direction in FIG. 2).

Further, when the protruding portion 4 has a convex shape, a surface of the convex tip of the protruding portion 4 is prevented projecting from a surface of the other tubular member. This configuration also increases a joining area between the tubular member 3 and the tubular member 5 as much as possible. This improves the joining strength between the tubular member 3 and the tubular member 5.

FIG. 3 shows a side view near the joining region of the junction structure 2 shown in FIGS. 1 and 2, and FIG. 4 shows the side view near the joining region in which the protruding portion 4 is shown in dotted lines.

As clearly shown in FIG. 4, the protruding portion 4 of the tubular member 3 or the tubular member 5 protrudes into the other tubular member.

It is noted that the protruding portions 4 are interchanged at a middle position of a laterally adjacent protrusion-depression in FIG. 4. That is, the resin of the tubular member 5 protrudes into the resin of the tubular member 3 to the left of the middle position, while the resin of the tubular member 3 protrudes into the resin of the tubular member 5 to the right of the middle position.

Figure 5:
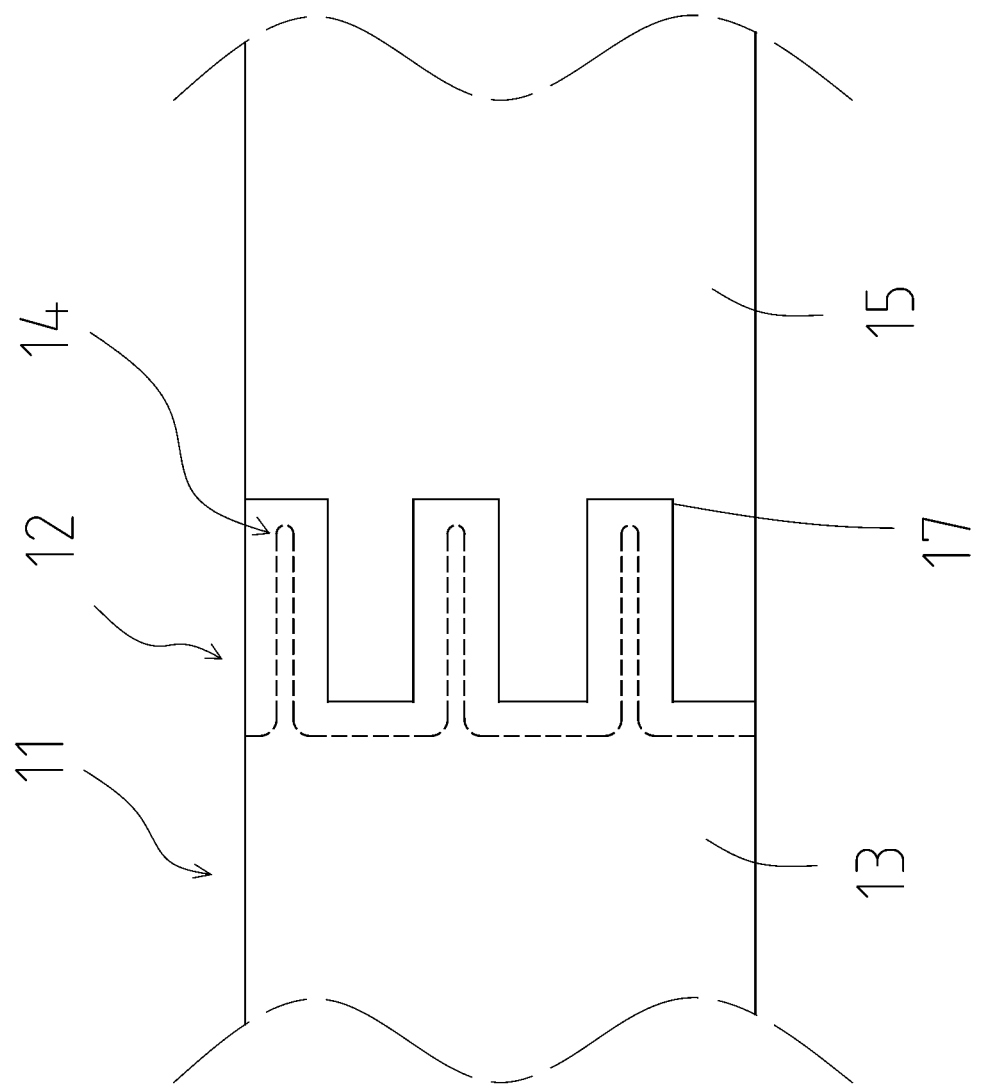
FIG. 5 shows a side view near a joining region in a junction structure according to the disclosed embodiments, where an inner protruding portion is shown in dotted lines.

FIG. 5 shows a side view near a joining region 12 of a junction structure 11 according to the disclosed embodiments.

With reference to FIG. 5, a tubular member 13 made of resin and a tubular member 15 made of resin are joined at the junction structure 11. An interface 17 between the tubular member 13 and the tubular member 15 at the joining region 12 has an uneven shape in the long axis direction along the circumferential direction of the tubular members 13, 15. This increases a joining area to enhance the joining strength between the tubular member 13 and the tubular member 15.

As in the joining region 2, the uneven shape of the joining region 12 in FIG. 5 is also approximately rectangular along the circumferential direction of the tubular members 13, 15.

In the junction structure 11, the tubular member 15 protrudes into the tubular member 13 along the entire circumferential direction. More specifically, in the junction structure 11, a protruding portion 14 of the tubular member 15 has a convex shape and protrudes into the tubular member 13 along the entire circumferential direction as shown in FIG. 5.

Therefore, in the junction structure 11, the joining strength between the tubular member 13 and the tubular member 15 can be improved even when a force is applied to the interface 17 between the tubular member 13 and the tubular member 15 in the radial direction.

Further, the protruding portion 14 of the tubular member 15 is formed to have a convex shape and protrudes into the tubular member 13 along the entire circumferential direction. This also increases a joining area between the tubular member 13 and the tubular member 15 as much as possible to improve the joining strength between the tubular member 13 and the tubular member 15.

Figure 6:
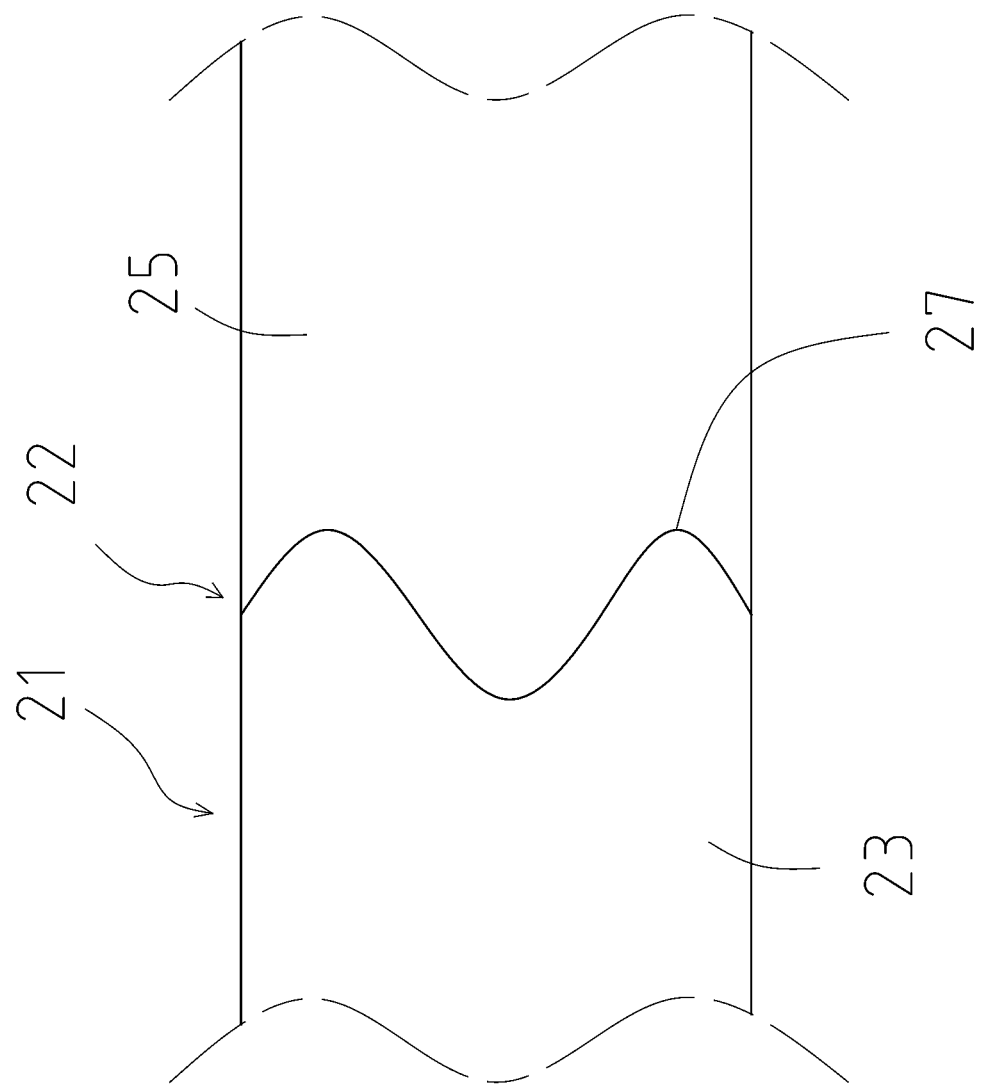
FIG. 6 shows a side view near a joining region of a junction structure according to the disclosed embodiments.
Figure 7:
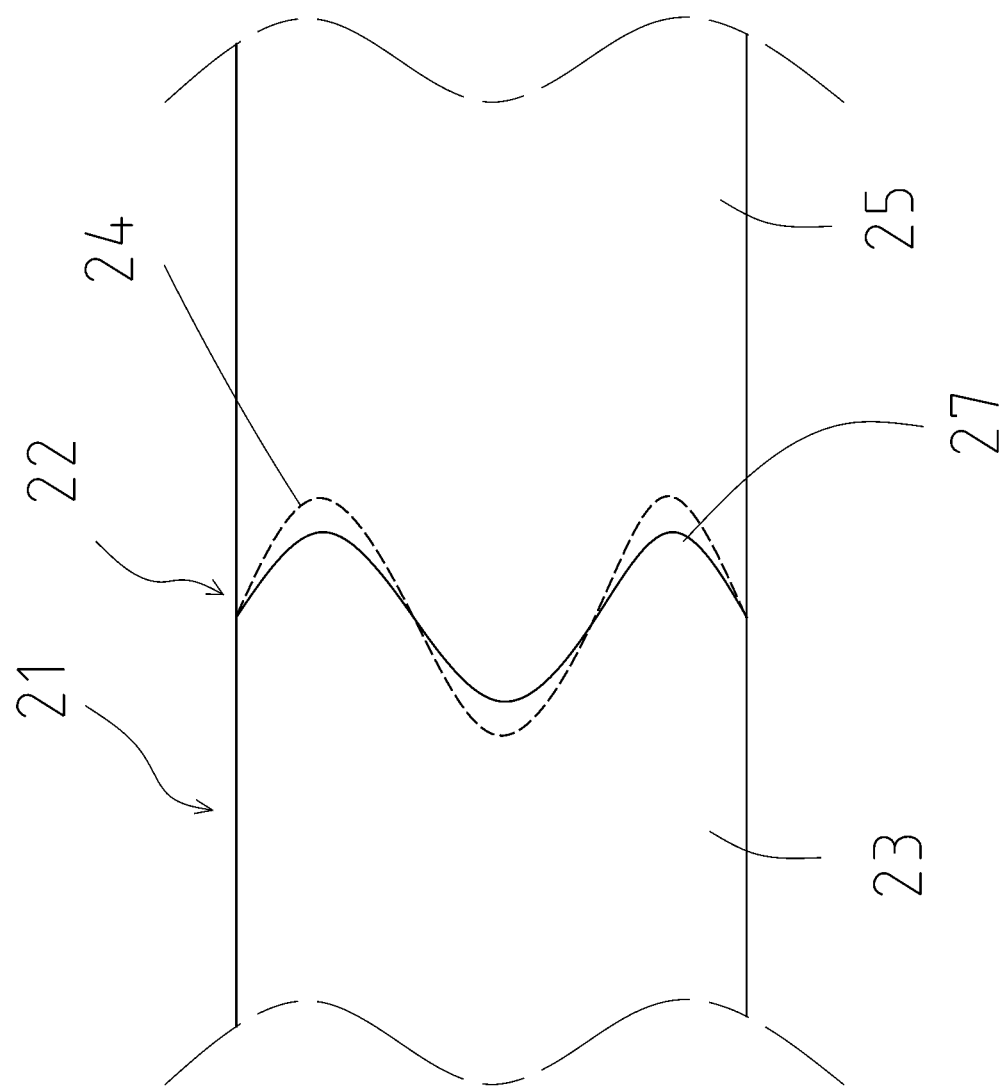
FIG. 7 shows the side view of FIG. 6 with an inner protruding portion shown in dotted lines.

FIG. 6 shows a side view near a joining region 22 of a junction structure 21 according to the disclosed embodiments, and FIG. 7 shows the side view of FIG. 6 with a protruding portion 24 drawn in dotted lines.

With reference to FIG. 6, a tubular member 23 made of resin and a tubular member 25 made of resin are joined at the junction structure 21. An interface 27 between the tubular member 23 and the tubular member 25 at the joining region 22 has an uneven shape in the long axis direction along the circumferential direction of the tubular members 23, 25 in order to increase a joining area between the tubular member 23 and the tubular member 25 as much as possible. This improves the joining strength between the tubular member 23 and the tubular member 25.

It is noted that the uneven shape of the joining region 22 is corrugated along the circumferential direction of the tubular members 23, 25, as shown in FIG. 6.

The interface 27 between the tubular member 23 and the tubular member 25 has a portion in which the tubular member 23 or the tubular member 25 includes the protruding portion 24 that protrudes into the other tubular member in a cross section. This improves the joining strength between the tubular member 23 and the tubular member 25 when a force is applied to the interface 27 between the tubular member 23 and the tubular member 25 in the radial direction.

More specifically, the protruding portion 24 of the tubular member 23 or the tubular member 25 has a convex shape and protrudes into the other tubular member only between an inner periphery and an outer periphery of the other tubular member. This prevents a surface of the convex tip of the protruding portion 24 from projecting from a surface of the other tubular member. It also further improves the joining strength between the tubular member 23 and the tubular member 25.

As clearly shown in FIG. 7, the protruding portion 24 of the tubular member 23 or the tubular member 25 protrudes into the other tubular member.

It is noted that the protruding portions 24 are interchanged at a middle position of a laterally adjacent protrusion-depression in FIG. 7. That is, the resin of the tubular member 25 protrudes into the resin of the tubular member 23 to the left of the middle position, while the resin of the tubular member 23 protrudes into the resin of the tubular member 25 to the right of the middle position.

Figure 8:
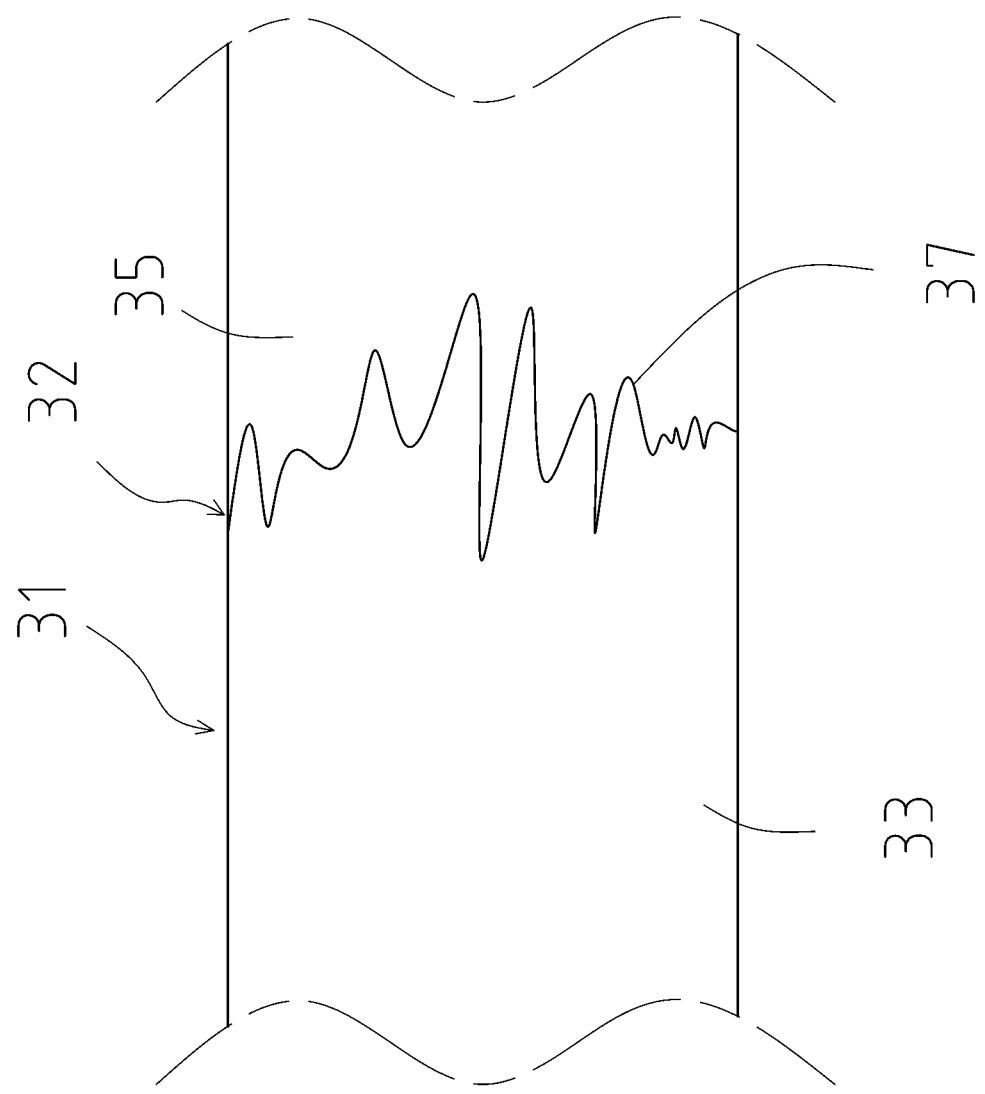
FIG. 8 shows a side view near a joining region of a junction structure according to the disclosed embodiments.
Figure 9:
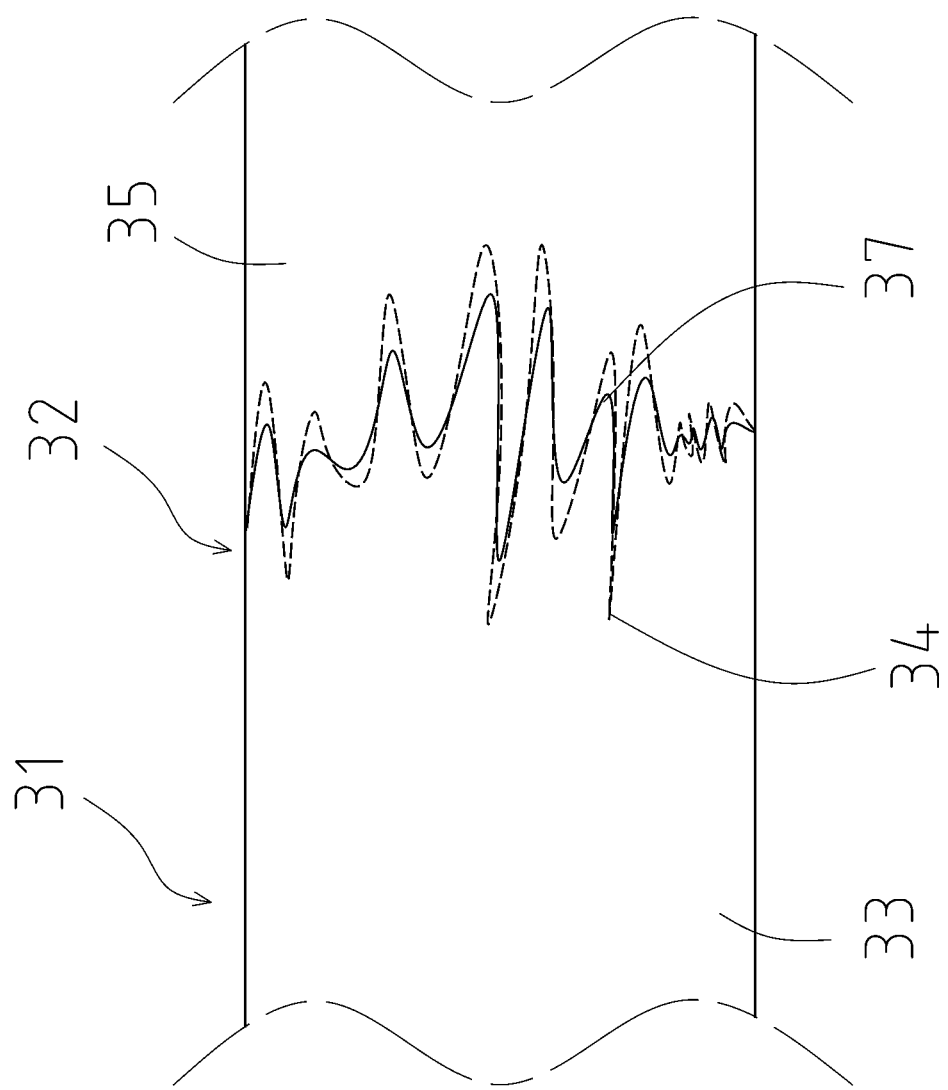
FIG. 9 shows the side view of FIG. 8 with an inner protruding portion shown in dotted lines.

FIG. 8 shows a side view near a joining region 32 of a junction structure 31 according to the disclosed embodiments, and FIG. 9 shows the side view of FIG. 8 with a protruding portion 34 drawn in dotted lines.

With reference to FIG. 8, a tubular member 33 made of resin and a tubular member 35 made of resin are joined at the junction structure 31. An interface 37 between the tubular member 33 and the tubular member 35 at the joining region 32 has an uneven shape in the long axis direction along the circumferential direction of the tubular members 33, 35 in order to increase a joining area between the tubular member 33 and the tubular member 35 as much as possible. This improves the joining strength between the tubular member 33 and the tubular member 35.

The interface 37 between the tubular member 33 and the tubular member 35 has a portion in which the tubular member 33 or the tubular member 35 includes the protruding portion 34 that protrudes into the other tubular member in a cross section. This improves the joining strength between the tubular member 33 and the tubular member 35 when a force is applied to the interface 37 between the tubular member 33 and the tubular member 35 in the radial direction.

More specifically, the protruding portion 34 of the tubular member 33 or the tubular member 35 has a convex shape and protrudes into the other tubular member only between an inner periphery and an outer periphery of the other tubular member. This prevents a surface of the convex tip of the protruding portion 34 from projecting from a surface of the other tubular member. It also further improves the joining strength between the tubular member 33 and the tubular member 35.

As clearly shown in FIG. 9, the protruding portion 34 of the tubular member 33 or the tubular member 35 protrudes into the other tubular member.

It is noted that the protruding portions 34 are interchanged at a middle position of a laterally adjacent protrusion-depression in FIG. 9. That is, the resin of the tubular member 35 protrudes into the resin of the tubular member 33 to the left of the middle position, while the resin of the tubular member 33 protrudes into the resin of the tubular member 35 to the right of the middle position.

Figure 10:
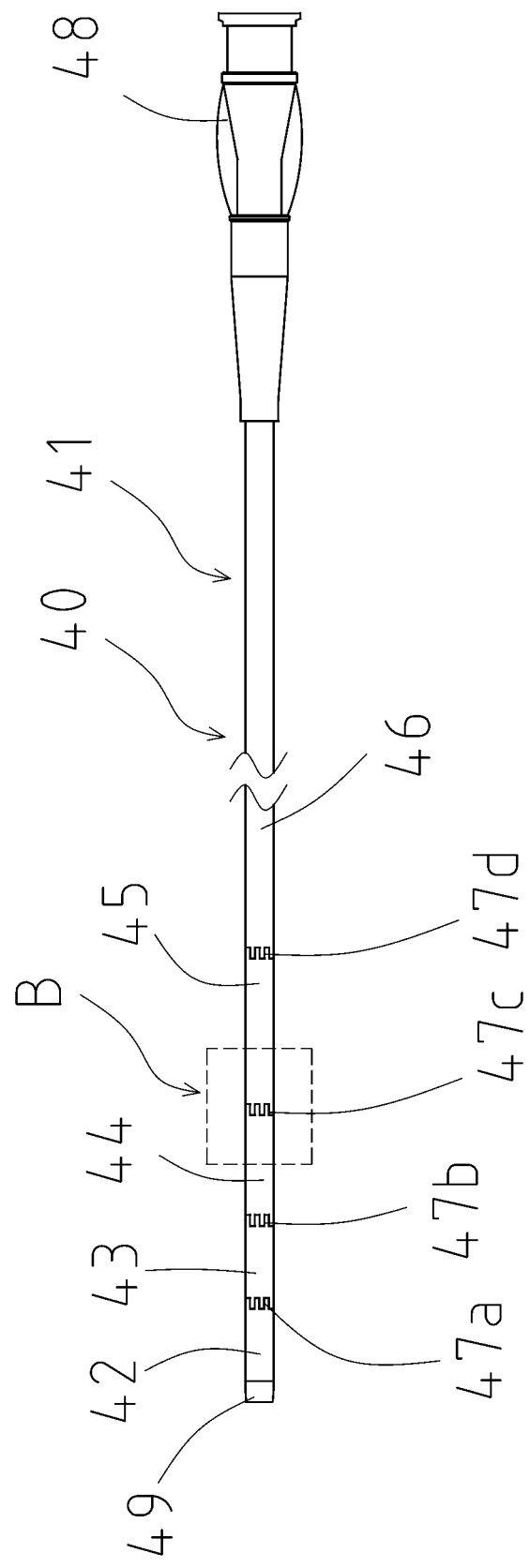
FIG. 10 shows an overall view of a catheter according to the disclosed embodiments.

FIG. 10 shows an overall view of a catheter 41 according to the disclosed embodiments.

With reference to FIG. 10, the catheter 41 includes a catheter tube body 40, a distal end tip 49 connected to a distal end of the catheter tube body 40, and a connector 48 connected to a proximal end of the catheter tube body 40.

The catheter tube body 40 includes multiple tubular members made of different resin materials and that are joined so that the catheter tube body 40 becomes increasingly more flexible toward the distal end from the proximal end. The catheter tube body 40 includes a tubular member 46, a tubular member 45, a tubular member 44, a tubular member 43, and a tubular member 42 in this order from the proximal end.

That is, the resin of the tubular member 46 is hardest, and the resin of each tubular member is softer in the order of the tubular member 45, the tubular member 44, the tubular member 43, and the tubular member 42. The resin of the tubular member 42 is softest.

The catheter tube body 40 includes the junction structure 1 (shown in FIGS. 1-4) at 4 positions, and includes an interface 47d, an interface 47c, an interface 47b, and an interface 47a in this order from the proximal end. The junction structures 1 further improve the joining strength between the tubular member 42 and the tubular member 43, the joining strength between the tubular member 43 and the tubular member 44, the joining strength between the tubular member 44 and the tubular member 45, and the joining strength between the tubular member 45 and the tubular member 46 by adding an improved joining strength against a pressure in the radial direction. This, in turn, improves the joining strength of the catheter tube body 40 as a whole.

Figure 11:
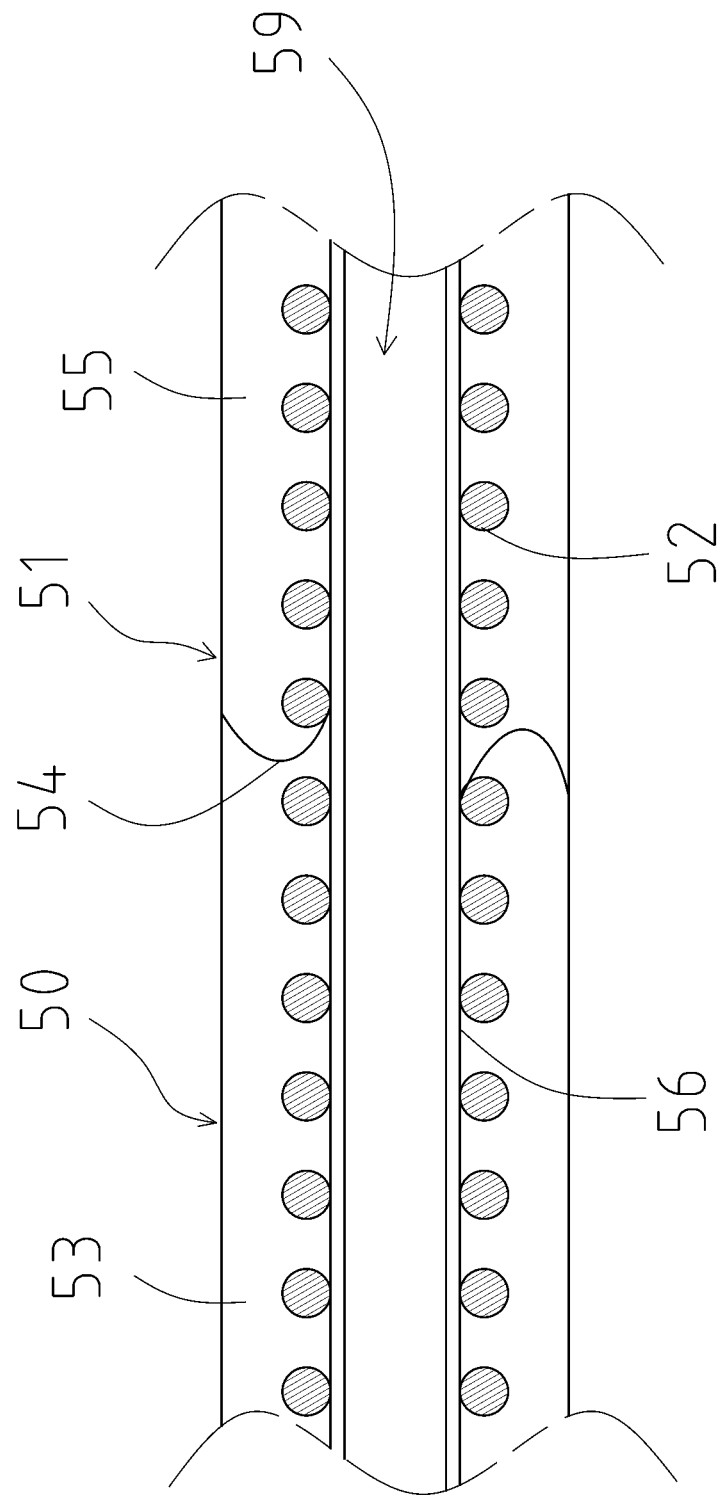
FIG. 11 shows a cross sectional view near a joining region of a catheter according to the disclosed embodiments.

FIG. 11 shows a cross sectional view (corresponding to the region B shown FIG. 10) near a joining region in a catheter 51 according to the disclosed embodiments.

It is noted that the catheter 51 includes a catheter tube body 50, a distal end tip (not shown) connected to a distal end of the catheter tube body 50, and a connector (not shown) connected to a proximal end of the catheter tube body 50, as in the catheter 41. Unlike the catheter tube body 40 of the catheter 41, however, the catheter tube body 50 is not a monolayer body. Instead, the catheter tube body 50 includes an inner layer 56, a coil body 52 wound around an outer periphery of the inner layer 56, and at least outer layers 53 and 55 covering outer peripheries of the inner layer 56 and the coil body 52. The catheter tube body 50 has an inner cavity 59.

The inner layer 56, the coil body 54, and the outer layers 53 and 55 are each tubular members, and the outer layers 53 and 55 are joined by the junction structure 1 discussed above.

Here, the outer layers 53 and 55 are formed such that a protruding portion 54 of one of the outer layers 53, 55 protrudes into the other outer layer only between an inner periphery and an outer periphery of the other outer layer, and the inner periphery of the other outer layer penetrates between individual coils (windings) of the coil body 52. This further enhances the joining strength between the outer layer 53 and the outer layer 55, which in turn improves the joining strength of the catheter tube body 50.

Further, in the catheter tube body 50, multiple tubular members (outer layers) made of different resin materials are joined so that the catheter tube body 50 becomes increasingly more flexible toward its distal end from its proximal end. For example, five tubular members may be joined together as in the catheter tube body 40 shown in FIG. 10. However, only the outer layer 55 and the outer layer 53 are shown in FIG. 11.

Figure 12:
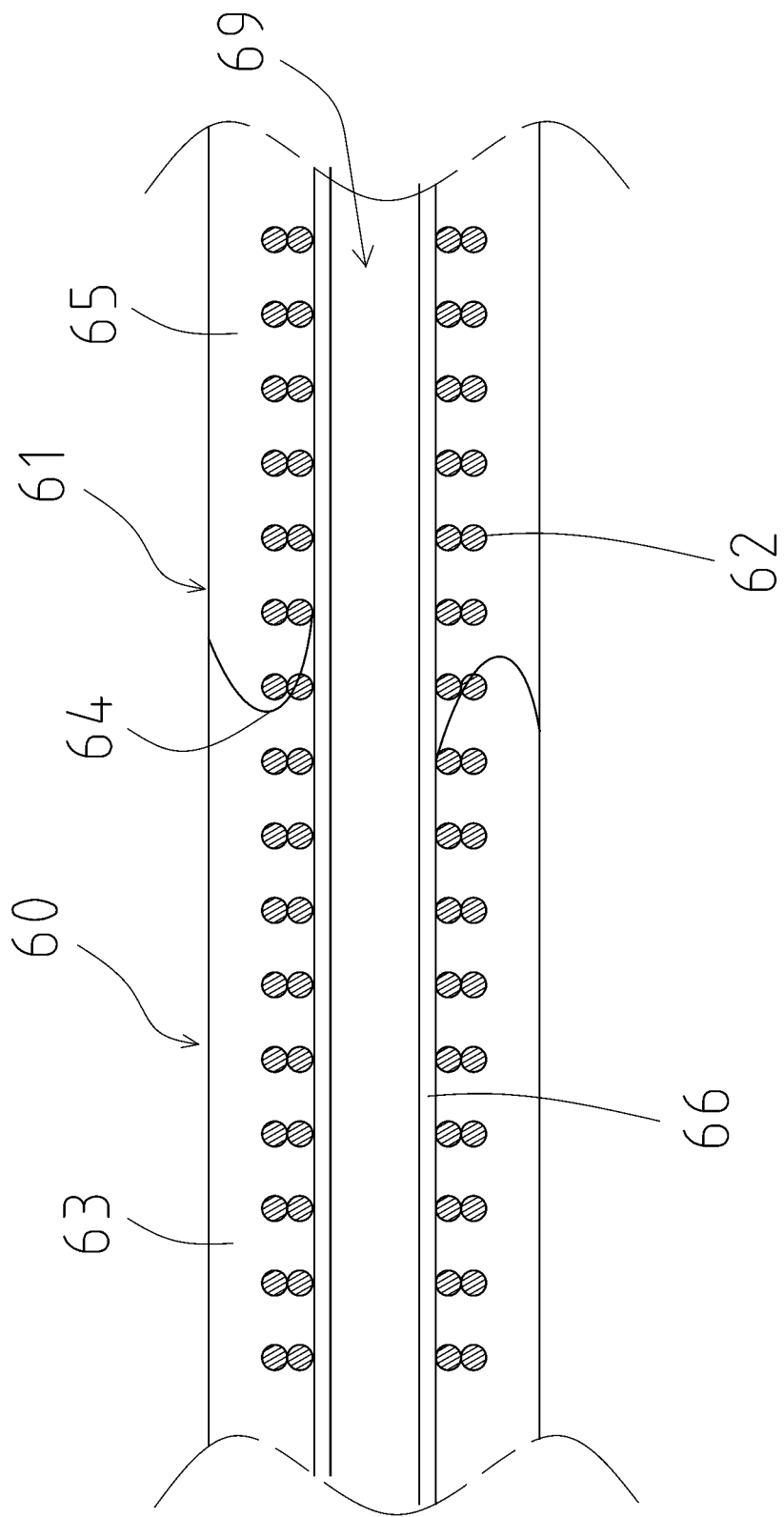
FIG. 12 shows a cross sectional view near a joining region of a catheter according to the disclosed embodiments.

FIG. 12 shows a cross sectional view (corresponding to the region B in FIG. 10) near a joining region in a catheter 61 according to the disclosed embodiments.

It is noted that the catheter 61 includes a catheter tube body 60, a distal end tip (not shown) connected to a distal end of the catheter tube body 60, and a connector (not shown) connected to a proximal end of the catheter tube body 60, as in the catheter 41.

Unlike the catheter tube body 40 of the catheter 41, however, the catheter tube body 60 is not a monolayer tubular body. Instead, the catheter tube body 60 includes an inner layer 66, a braid 62 disposed around an outer periphery of the inner layer 66, and outer layers 63 and 65 covering outer peripheries of the inner layer 66 and the braid 62. The catheter tube body 60 has an inner cavity 69.

The inner layer 66, the braid 62, and the outer layers 63 and 65 are each tubular members, and the outer layers 63 and 65 are joined by the junction structure 1 discussed above.

Here, the outer layers 63 and 65 are formed such that a protruding portion 64 of one of the outer layers 63, 65 protrudes into the other outer layer only between an inner periphery and an outer periphery of the other outer layer, and an inner periphery of the outer layer 63 or the outer layer 65 penetrates into the braid 62. This further enhances the joining strength between the outer layer 63 and the outer layer 65, which in turn improves the joining strength of the catheter tube body 60.

Further, in the catheter tube body 60, multiple tubular members (outer layers) made of different resin materials are joined so that the catheter tube body 60 becomes increasingly more flexible toward its distal end from its proximal end. For example, five tubular members may be joined together as in the catheter tube body 40. However, only the outer layer 65 and the outer layer 63 are shown in FIG. 12.

Various junction structures and catheters having the junction structures are described above, but the present invention shall not be limited to those embodiments. Various modifications may be made without departing from the spirit and scope of the present invention.

For example, the catheters described above include the junction structure 1 shown in FIGS. 1-4, but the junction structure 11, the junction structure 21, or the junction structure 31 may be used. In these cases, the catheter tube body 40, the catheter tube body 50, and the catheter tube body 60 can benefit from the aforementioned effects expected from the junction structures used.

Further, the catheters described above have five joined tubular members. However, the number of tubular members is not limited to five, and any number of tubular members may be used.

What is claimed is:

1. A junction structure comprising:
   a first tubular member; and
   a second tubular member joined end-to-end with the first tubular member, wherein:
   an interface between the first tubular member and the second tubular member has an uneven shape in a longitudinal direction of the junction structure on a surface of the first tubular member and the second tubular member along a circumferential direction of the first tubular member and the second tubular member, and
   one of the first tubular member and the second tubular member includes a protrusion along the uneven shape, and the entire protrusion protrudes into the other one of the first and second tubular members only in a region between an inner circumferential surface and an outer circumferential surface of the other one of the first and second tubular members so that the protrusion is sandwiched by the inner circumferential surface and the outer circumferential surface, wherein the protrusion protrudes in both the longitudinal direction and the circumferential direction.

2. The junction structure according to claim 1, wherein the protrusion protrudes into the other one of the first and second tubular members along an entire circumferential region having the uneven shape.

3. A catheter comprising the junction structure according to claim 2.

4. A catheter comprising:
   an inner layer;
   a reinforcing layer disposed around an outer periphery of the inner layer; and
   the junction structure according to claim 2 as an outer layer covering the outer periphery of the inner layer and an outer periphery of the reinforcing layer,
   wherein an inner periphery of the other one of the first and second tubular members penetrates into the reinforcing layer.

5. The junction structure according to claim 2, wherein the protrusion has a continuously convex shape in cross-sectional view between the inner circumferential surface and the outer circumferential surface.

6. A catheter comprising the junction structure according to claim 5.

7. The junction structure according to claim 1, wherein the protrusion has a continuously convex shape in cross-sectional view between the inner circumferential surface and the outer circumferential surface.

8. A catheter comprising the junction structure according to claim 7.

9. A catheter comprising the junction structure according to claim 1.

10. A catheter comprising:
    an inner layer;
    a reinforcing layer disposed around an outer periphery of the inner layer; and
    the junction structure according to claim 1 as an outer layer covering the outer periphery of the inner layer and an outer periphery of the reinforcing layer,
    wherein an inner periphery of the other one of the first and second tubular members penetrates into the reinforcing layer.

* * * * *